United States Patent [19]

Maekawa et al.

[11] 4,132,527

[45] Jan. 2, 1979

[54] DIAGNOSTIC COMPOSITIONS, DIAGNOSING INSTRUMENTS, AND METHODS OF MANUFACTURING SAME

[75] Inventors: Hideyuki Maekawa, Osaka; Kaoru Ishitobi, Yao, both of Japan

[73] Assignee: Shionogi & Co., Ltd., Osaka, Japan

[21] Appl. No.: 708,631

[22] Filed: Jul. 26, 1976

Related U.S. Application Data

[62] Division of Ser. No. 536,867, Dec. 27, 1974, Pat. No. 3,971,702.

[30] Foreign Application Priority Data

Jan. 9, 1974 [JP] Japan .................................... 49-5805
Mar. 3, 1974 [JP] Japan .................................... 49-27298

[51] Int. Cl.² ...................... C07C 87/28; C07C 87/64; G01N 31/22; G01N 33/16
[52] U.S. Cl. ................................... 23/230 B; 252/408; 260/576; 422/56
[58] Field of Search ...................... 23/230 B, 253 TP; 260/576; 252/408

[56] References Cited

U.S. PATENT DOCUMENTS

| 2,290,436 | 7/1942 | Kamlet | 23/230 B |
| 2,981,606 | 4/1961 | Keston | 23/253 TP X |
| 3,012,976 | 12/1961 | Adams, Jr. et al. | 23/253 TP X |
| 3,123,443 | 3/1964 | Smeby | 23/253 TP |
| 3,266,868 | 8/1966 | Harvill | 23/253 TP |

OTHER PUBLICATIONS

Rassow et al., Chem. Abstr. 6, 789 (1912).

Primary Examiner—Robert M. Reese
Attorney, Agent, or Firm—Birch, Stewart, Kolasch and Birch

[57] ABSTRACT

A diagnostic composition containing as a chromogen a diamino-biphenyl derivative in which at least one of the hydrogen atoms in the amino groups thereof is replaced by a lower alkyl group by reaction with an alkylating agent. The diagnosing instrument is prepared by impregnating a bibulous, porous support in a solution comprising the diagnostic composition and optionally a saccharide oxidase, peroxidase and a guaiac, and, if necessary, a buffer, a surfactant, a background adjusting dye and/or an agent for increasing the viscosity of the composition. This diagnosing instrument can be handled in a simple and convenient way and is used to identify semi-quantitatively a saccharide in body fluids or excrements of humans or animals with reliability.

29 Claims, No Drawings

DIAGNOSTIC COMPOSITIONS, DIAGNOSING INSTRUMENTS, AND METHODS OF MANUFACTURING SAME

This application is a Divisional of copending application Ser. No. 536,867, filed on Dec. 27, 1974, now U.S. Pat. No. 3,971,702.

The present invention relates to a diagnostic composition, a diagnosing instrument and a method of manufacturing the same. More particularly, it relates to a diagnostic composition into which a bibulous, porous support is impregnated to form a diagnosing instrument for use in making a diagnosis of diseases or disorders of physiological conditions of humans or animals. It also relates to a method of manufacturing the diagnosing instrument.

Examination of body fluids or excrements of humans or animals such as blood, urine or solid excrements plays an important role in diagnosing diseases or examining and evaluating the effects of treatment of diseases with medicine. For identifying the components of a blood sample, however, the separation of the erythrocyte from the blood sample is required prior to examination and the pretreatment to take the plasma and serum components from the blood sample requires the skilled work of experienced personnel and extensive equipment. Therefore, diagnostic compositions and diagnosing instruments which can be employed and handled in a simple and convenient manner and, furthermore, give diagnostic test results semi-quantitatively with reliability have hithertofore been desired. A method of manufacturing such diagnosing instruments has also been desired.

Various attempts have been made to develop a simple and convenient means for diagnostic use. Recently, a diagnosing instrument such as a test strip which is composed of a sheet of testing paper has frequently been used for this purpose. For example, U.S. Pat. No. 3,092,465, British Pat. No. 922,665, Japanese Patent Publication No. 14,673/1969, and Japanese Patent Publication No. 15,669/1970 disclose such an instrument which can be used for identifying and determining glucose, galactose, phenylalanine, or urea in a blood sample. Some of such instruments have been marketed, for example, as Dextrostix (registered trade name of Miles Laboratories, Inc.).

The diagnosing instruments such as a test strip which have conventionally been employed for identifying saccharides in urea or blood may be prepared, for example, by impregnating a bibulous, porous support such as filter paper into an enzymatic system or a chromogen and then drying the impregnated support. It is convenient to use such a test strip because, when it is dipped in a liquid sample to be examined, a substance to be identified is detectable by a color development or change of said enzymatic system or chromogen which is induced by a reaction product formed when the enzymatic system is brought into contact with the substance in the presence of oxygen. However, it is unavoidable that the stability of color development and the hue to be produced by the chromogen is affected by the pH value of the liquid sample or the amount of inhibiting materials present in the sample, thereby making it difficult to give a reliable test result. Accordingly, conventional diagnostic compositions and diagnosing instruments containing benzidine or a homolog thereof such as ortho-tolidine can achieve only a limited performance for diagnostic purposes.

In order for a diagnosing instrument to permit a smooth enzymatic reaction whereby a clear and stable color development or color change of a chromogen present therein is brought about, it is necessary to maintain the stability of the chromogen in a system where the chromogen is converted to produce a color and to keep the pH value of a liquid sample in a particular range. For this purpose, the chromogen is required to serve as a hydrogen donor for an oxidation-reduction reaction system, that is, in which the chromogen is converted into a product which can readily act with saccharides in urine or catalase in solid excrements for producing a color. At the same time, the chromogen is also required to function to determine at least semi-quantitatively a substance to be identified in a liquid sample by development of or conversion into a color by autoxidation.

Said conventional diagnosing instruments are prepared in such a manner that a translucent, thin coating film or a water-repellent or hydrophobic material is coated on the surface of the diagnosing test strip in order for the haemoglobin or erythrocyte of a blood sample not to come into its porous support while being dipped in a test sample so that the haemoglobin remaining on the surface thereof can readily be washed away by running waters in a particular period of time after the test strip is dipped in the sample to be examined. Said conventional diagnosing instruments are convenient in this respect. However, coating the support uniformly with a water-repellent material is difficult. And the non-uniformity of such a coating on the surface of the test strip may cause irregularities in determination of a substance to be identified or difficulty in carrying out a semi-quantitative analysis with reliable results because the state of the coating may affect the reliability of determination and identification.

Accordingly, it is an object of the present invention to provide a diagnostic composition which can give a stable color development or color change or a hue of the color produced by the conversion of a chromogen. Another object of the present invention is to provide a diagnostic composition which can give a reliable, semi-quantitative test result in determining and identifying a saccharide in body fluids or excrements of humans or animals. Another feature of the present invention is a diagnosing instrument containing such a diagnostic composition which can be used and handled in a simple and convenient manner and which enables a semi-quantitative analysis for a saccharide in body fluids or excrements of humans or animals with reliability. A further feature of the present invention is a method of manufacturing such a diagnosing instrument. Other objects, features and advantages of the present invention will become apparent during the course of the description of the specification and the claims.

It has been found that a diagnostic composition which can obviate the disadvantages and difficulties of said conventional diagnostic compositions can be provided comprising a diamino-biphenyl derivative in which at least one of the hydrogen atoms in the amino groups thereof is replaced by a lower alkyl group by treatment with an alkylating agent. The alkylated diamino-biphenyl derivative has also been found to give the corresponding oxidized product which can be converted to develop and produce a clear color and which can also give a more stable shade in a higher pH range than the diamino-biphenyl derivative bearing no alkyl substitution in either of the amino groups thereof.

The alkylated diamino-biphenyl derivative may be prepared by treatment of the diamino-biphenyl derivative having no alkyl substitution in the amino groups thereof with an alkylating agent. The reaction may be carried out at ambient or elevated temperature. The diamino-biphenyl derivative to be used as a starting material is benzidine and a homolog thereof having at least on substituent in the alkyl or alkoxy series with from one to two carbon atoms and its includes, for example, benzidine, tolidine and dianisidine, benzidine, ortho-tolidine and ortho-dianisidine being preferred. The alkylating agent which can be used for this purpose may be any agent which can usually be employed for alkylating an amino group and which can also produce the diamino-biphenyl derivative in which at least one of the hydrogen atoms in the amino groups thereof are to be substituted by a lower alkyl group having from one to four carbon atoms and preferably from one to two carbon atoms. Illustrative examples of the alkylating agents are a dialkyl sulfate such as, for example, dimethyl sulfate and diethyl sulfate, an alkyl halogenide such as, for example, methyl chloride, methyl bromide, methyl iodide, ethyl chloride, ethyl bromide and ethyl iodide, and a dialkyl sulfoxide such as, for example, dimethyl sulfoxide, diethyl sulfoxide and methylethyl sulfoxide. The alkylation of the diamino-biphenyl derivative by treatment with said alkylating agent can usually produce a reaction product in which at least one of the hydrogen atoms in the amino groups thereof is substituted by a lower alkyl group. And said alkylation may also produce a mixture of the alkylated diamino-biphenyl derivatives in which the two amino groups thereof are each alkylated with up to two alkyl groups. Furthermore, the alkylation reaction usually gives these reaction products having a different degree of alkyl substitution in admixture with the starting material. However, the use of such a mixture does not affect adversely the diagnostic effect, so that it is not necessary to separate the alkylated reaction product having the same alkyl substitution from that of different alkyl substitutions or to separate a mixture of the alkylated reaction products from the starting material which remains unreacted in the reaction mixture. In view of the technical difficulty in separating the unreacted starting material from a mixture of the alkylating products, it is rather advisable from the practical point of view to use a total mixture containing the starting material and the variously alkylated products.

The alkylated diamino-biphenyl derivative to be used in the present invention can provide its own particular color shade according to the number and/or the position of alkyl substitution in the amino groups thereof. Accordingly, a particular and desired diagnosing instrument comprising the diamino-biphenyl derivative with an appropriate amount of alkyl substitution in an appropriate position of the amino groups thereof can be chosen according to the kind and nature of a substance to be identified and a liquid to be examined.

It has also been found that a diagnosing instrument comprising said alkylated compound, a bibulous, porous support and an oxidation-reduction indicator capable of a reaction with a saccharide to be identified such as glucose, the support being impregnated in a solution containing said alkylated compound and thereby a thin, translucent film or a water-repellent or hydrophobic agent being formed on the surface thereof, can alleviate the disadvantages and the difficulty involved in said conventional diagnosing instruments. The diagnosing instrument of the present invention comprises said alkylated diamino-biphenyl derivative, and, when desired and preferably, together with a saccharide oxidase, peroxidase and guaiacum, supported on a bibulous, porous support.

By the term "saccharide oxidase" referred to herein is meant any enzyme which possesses the ability to oxidize a saccharide such as, for example, glucose and galactose and which can identify the saccharide to be determined in a liquid sample at least semi-quantitatively. The saccharide oxidase includes, for example, glucose oxidase and galactose oxidase.

A guaiac, one of the components to be used in the diagnosing instrument of the present invention, may generally be of natural origin. It is difficult to identify the composition thereof exactly, but the guaiac to be used for the present purpose may be in the form of a yellowish brown, amorphous powder and includes alpha-guaiaconic acid ($C_{22}H_{26}O_6$) or beta-guaiaconic acid ($C_{21}H_{26}O_5$). The chloroform-soluble portion of guaiac which is commercially available may usually be used for the present invention simply for convenience in availability.

The bibulous, porous support to be used for the diagnosing instrument of the present invention may generally be a filter paper, particularly hardened filter paper, preferably Whatman No. 50, Whatman No. 52 Whatman No. 54, Whatman No. 540, Whatman No. 541, Whatman No. 542 and Whatman DE-81, Whatman No. 54 being more preferred. A sintered porous material of glass or plastic materials which can carry an adsorbent in its fine hollows or cavities may also be used for this purpose.

The diagnostic composition and the diagnosing instrument of the present invention possess excellent properties in producing or developing a color with stability and in not being impaired by inhibiting materials present in a liquid sample to be examined. They can also improve the homogeneity of the chromogenic or coloring reaction which takes place on the diagnosing instrument and enhance the sensitivity of the chromogen with preciseness.

The alkylated diamino-biphenyl derivative to be used for the present invention is in the form of oils, while the non-alkylated diamino-biphenyl derivative to be used as a starting material for the preparation of the alkylated compounds of the present invention is in the form of crystals. If the starting material is left unreacted in the reaction mixture and it is present together with the oily alkylated products, such a mixture can remain in the form of an oily material. Furthermore, the starting material which is left unreacted in the reaction mixture does not deposit on the surface of the support as solids so that the disadvantages to be expected from the solids deposited on the surface thereof are eliminated. Such a mixture is also compatible with the guaiac in the diagnostic composition of the present invention, thereby functioning to prevent the haemoglobin present in a body fluid or excrement sample to come into the porous support.

The diagnostic composition of the present invention may contain any component which can conventionally be used for this purpose, such as a buffer, a surfactant, a background adjusting dye and/or an agent for increasing the viscosity of the composition. The buffer includes, for example, an aqueous solution of phthalic acid, a phosphate or citric acid. The surfactant includes, for example, a complex mixture of polyoxyethylene ethers of mixed esters of fatty acids, e.g., Tween 20 (registered trade name). The background adjusting dye includes, for example, tartrazine. The agent for increasing the viscosity thereof includes, for example, a protecting colloid which is in general employed for stabilization of an enzyme, such as polyalkylene glycol and polyvinyl alcohol.

The method of manufacturing the diagnosing instrument of the present invention comprises impregnating said bibulous, porous support in a solution containing the alkylated diamino-biphenyl derivative of the present invention. The method of manufacturing the diagnosing instrument of the present invention may vary depending upon the purpose for which it is employed. In a case where a saccharide oxidase, peroxidase and a guaiac may optionally be added to the impregnating solution, the impregnation may preferably be effected at two stages, and the diagnosing instrument thus prepared can provide a good overall performance for diagnostic purposes. The first step comprises impregnating said bibulous, porous support in a solution containing a saccharide oxidase and peroxidase and drying the impregnated support. And the second step involves impregnating the previously impregnated, dry support in another solution which contains the alkylated diamino-biphenyl derivative and a guaiac and drying the twice impregnated support. The method thereof according to the present invention is not limited to said specific embodiment for carrying out the present invention and should be construed as including another embodiment in which a mixture of said four components is present all together or in different combinations thereof. Said buffer, surfactant, background adjusting dye and/or agent for increasing the viscosity may also be added to the impregnating solutions at a desired stage. In some cases, the diagnosing instrument of the present invention may be manufactured by impregnating said bibulous, porous support in a solution containing the alkylated diamino-biphenyl derivative and, when desired, said buffer, surfactant, background adjusting dye and/or agent for increasing the viscosity. The diagnosing instruments prepared by the method of the present invention can also show an excellent property in controlling and preventing the penetration of the haemoglobin of a liquid sample to be examined.

The diagnosing instruments of the present invention may be employed in a conventional manner. A droplet of a blood sample is dropped on the surface of a test strip and the blood sample remaining thereon is washed away with water in a particular period of time for test determination. The diagnosing instruments of the present invention can enable the ready removal of a stain caused by the blood sample which affects adversely the test determination, although said conventional test strips are insufficient in removing a stain to such an extent that the stain does not impair the color reaction whereby the accuracy of test results are achieved. Thus, the diagnosing instruments of the present invention can give an accurate and reliable test result without undergoing the adverse effect of the stain which otherwise impairs the test accuracy. These advantageous properties which the diagnosing instruments of the present invention show in actual practical application makes it possible to identify and determine a substance to be identified in an at least semi-quantitative manner and they can cause the coloring reaction on the surface thereof to take place in a stable manner. The diagnosing instruments of the present invention can identify semi-quantitatively a saccharide in body fluids or excrements of humans or animals, for example glucose in an amount of 0 to about 500 mg. per dl. It is without doubt to be noted that when the other saccharide oxidase, for example, galactose oxidase, is used instead of glucose oxidase, the diagnosing instruments of the present invention can present substantially the same results as obtained with said diagnosing instrument wherein glucose oxidase is employed.

The following references and examples illustrate the present invention in more detail without, however, limiting the same thereto. It should be understood that the amount of the components with which a support is coated should not be limited to the amounts thereof described in the following examples and, particularly, the amounts of the N-(and/or N'-) methylated or ethylated diamino-biphenyl derivatives and the guaiac which are the major components of a solution to be used for said second impregnation step should be construed as being capable of being altered and varied generally within the range of tolerance of plus or minus about 50 percent relative to the amounts described in any of the following examples from the consideration of the stability of a particular enzyme to be used and the range in which the determination is made with reliability. Furthermore, the amounts of the saccharide oxidase which may preferably be used for a solution of the first impregnation step may be varied and altered in proportion to the variation in the amounts of the components of the solution for the second impregnation step.

The following reference examples involve the preparation of the alkylated derivatives.

REFERENCE EXAMPLE 1

To a solution of 0.1 g. of ortho-tolidine in 2.0 ml. of benzene was added 0.6 g. of dimethyl sulfate (1 mole) and the mixture was left to stand for 30 minutes at room temperature. The amine compound was caused to be transferred into the benzene layer as 10 ml. of a 10 percent sodium hydroxide aqueous solution was added to the mixture. The benzene layer was washed with water and benzene was distilled off to give oily materials containing the starting material and a mixture of five kinds of the reaction products having a different degree of methyl substitution.

REFERENCE EXAMPLE 2

The procedure of Reference Example 1 was repeated except that 10 ml. of methanol and 1.5 g. of ethyl iodide (2 moles) were used instead of 2.0 ml. of benzene and 0.6 g. of dimethyl sulfate, respectively, and the reaction was carried out for 1 hour. The reaction mixture was extracted with 20 ml. of benzene and worked up in the same manner as above to give a mixture of the starting material and five kinds of the reaction products having a different degree of ethyl substitution.

REFERENCE EXAMPLE 3

To a solution of 1.0 g of benzidine in 40 ml. of benzene was added 1.4 g. of dimethyl sulfate (2 moles) and the mixture was left to stand for 30 minutes at room temperature. After addition thereto of 30 ml. of a hot 10 percent sodium hydroxide aqueous solution, the solution was made neutral and fractioned. The benzene layer was then washed with water, and benzene was distilled off to give the reaction products with a mixture of the methylated benzidine derivatives. A small amount of the starting material was also left unreacted.

REFERENCE EXAMPLE 4

The procedure of Reference Example 3 was repeated except that 20 ml. of methanol and 1.5 g. of methyl iodide (2 moles) were used and the mixture was stirred for 1 hour at room temperature. The mixture was made neutral with 1 g. of granulated sodium hydroxide, and methanol was distilled off. The resulting material was extracted with a mixture of 100 ml. of benzene and 20 ml. of water, and the extract was fractioned and worked up in the same manner as above to give products similar to the products as above.

It is to be noted that the ratio of the compounds in a mixture of the compounds depends upon the reaction operations and conditions. For examples, the ratio of the compounds of Reference Example 1 was determined by measuring the peaks obtained by gas chromatography, and was found to be as follows:

| Compounds | Percent Amounts |
|---|---|
| Ortho-tolidine | 37.9 |
| N-monomethylated | 43.4 |
| N,N'-dimethylated | 7.5 |
| N,N-dimethylated | 8.6 |
| N,N,N'-trimethylated | 2.6 |
| N,N,N',N'-tetramethylated | trace. |

The following tables show the colors obtained by the coloring reaction of the alkylated amine derivatives. Table 1 indicates the example of the coloring reaction of ortho-tolidine and its various methylated derivatives obtained in Reference Example 1, and Table 2 shows the coloring reaction of benzidine and its various methylated derivatives obtained in Reference Example 3.

Table 1

| Compounds | Colors |
|---|---|
| Ortho-tolidine | Blue |
| N-Monomethylated | Slightly greenish blue |
| N,N-Dimethylated | No color development |
| N,N'-Dimethylated | Bluish green |
| N,N,N'-Trimethylated | Green |
| N,N,N',N'-Tetramethylated | Green (The color development was late.) |

All the methylated benzidine derivatives can be converted into the corresponding oxidized products which can produce a more stable color development in a higher pH range than ortho-tolidine itself.

Table 2

| Compounds | Colors |
|---|---|
| Benzidine | Dark blue |
| N-monomethylated | Dark blue |
| N,N-dimethylated | Bluish green |
| N,N,N'-Trimethylated | Green |
| N,N,N',N'-tetramethylated | Yellowish green |

The mixture of the ethylated ortho-tolidine derivatives produced in Reference Example 2 was developed on a thin layer chromatogram and the coloring reaction was examined, resulting in almost the same coloring reaction as produced with the mixture of the methylated derivatives of Reference Example 1.

The following examples illustrate the preparation of the diagnosing instruments of the present invention.

EXAMPLE 1

Two different kinds of impregnating solutions having the following compositions were prepared in a conventional manner.

The composition of the solution to be used for the first impregnation step was as follows:

| Composition | Amounts |
|---|---|
| 0.5 M phthalic acid buffer solution (pH 5.3) | 13 ml. |
| Glucose oxidase | 1,000 units |
| Peroxidase 6 mg. | |
| Tartrazine | 4.2 mg. |
| Polyvinyl alcohol | 200 mg. |

The solution for the second impregnation procedure has the following composition:

| Composition | Amounts |
|---|---|
| Mixture of methylated ortho-tolidines (product of Reference Example 1) | 80 mg. |
| Guaiac (chloroform-soluble portion) | 100 mg. |
| Ethanol | 13 ml. |

A test strip was prepared by dipping a piece of Whatman No. 54 filter paper in said solution for the first impregnation step, drying the impregnated paper, dipping again the dry paper in said solution for the second impregnation step and drying the twice impregnated paper. The piece of the dry filter paper was cut to a width of 5 mm. and stored in a place where no direct light was shed on it and the moisture was maintained at a low value.

In using the test strip prepared above for identification and determination of glucose in a blood sample, for example, a droplet of the blood sample was dropped on the surface of the test strip and the haemoglobin remaining thereon was washed away by flowing water against the surface of the test strip for 1 minute. The test strip gave the coloring reaction in proportion to the concentration of glucose in the blood samples. The color development was then caused to take place and compared with a standard color shade index to carry out the semi-quantitative comparative analysis. The standard color shade index was prepared by developing and determining a color in proportion to a specified amount of glucose in a blood sample. For the test strips of the present invention, no color deterioration was observed 5 minutes after being washed with various amounts of waters as usually seen with respect to said conventional test strips commercially available.

EXAMPLE 2

A test strip was prepared in substantially the same manner as in Example 1 except for the employment of the ethylated ortho-tolidine mixture prepared in Reference Example 2 instead of the methylated ortho-tolidine derivatives in the second solution. The test strip was found to show almost the same results as with the test strip prepared in Example 1.

COMPARATIVE EXAMPLE

A test strip was prepared in substantially the same manner as in Example 1 except that non-reacted ortho-tolidine was employed instead of the methylated ortho-tolidine mixture. The test strip, when employed for diagnostic purposes, was not uniform in the coloring reaction and it was also insufficient in removing the haemoglobin adhered to the surface of the test strip, so that the test results were unsatisfactory as compared with the test strips prepared in Examples 1 and 2.

EXAMPLE 3

The test strips were prepared in the same manner as in Example 1 except that chloroform, methylene chloride, tetrachlorocarbon or dichloroethane was each employed instead of ethanol in the solution for the second impregnation step. These test strips were also found to give almost the same results as the test strip obtained in Example 1.

The following examples illustrate the preparation of test strips useful for identifying and determining saccharides and the occult bleeding in urine, respectively.

EXAMPLE 4

Various impregnating solutions were prepared using the following composition:

| Composition | Amounts |
| --- | --- |
| Mixture of the reaction products from ortho-tolidine or benzidine (as prepared in Reference Examples) | 20 – 100 mg. |
| 95% Ethanol | 4 – 6 ml. |
| 0.1 M – 0.5 M citric acid buffer solution (pH 4 – 8) | 2 – 3 ml. |
| Glucose oxidase | 500 – 2,000 units |
| Tartrazine | 0.5 – 15 mg. |
| Tween 20 (10%) | 0 – 0.1 ml. |
| Peroxidase | 1 – 10 mg. |

Solutions having said compositions were prepared, for example, by dissolving 60 mg. of a mixture of said reaction products in 6 ml. of ethanol, adding thereto 3 ml. of the buffer solution; dissolving a mixture of 1,000 units of glucose oxidase, 1 mg. of peroxidase and 10 mg. of tartrazine in 4 ml. of the buffer; mixing said two solutions with each other; and adding thereto 0.1 ml. of Tween 20.

For comparative purposes, solutions containing non-reacted ortho-tolidine or benzidine were prepared in the same manner as above.

A test strip was then prepared by dipping a support such as filter paper in said solution and drying the impregnated paper by flowing current of air having a temperature of 70° C. for 3 minutes. The test strips produced as above were as follows:

Test strip A: This test strip contains reaction products prepared in Reference Example 1 or a mixture of the reaction products prepared in Reference Example 2.

Test strip B: The test strip contains ortho-tolidine which is not reacted by any alkylating agent and was used as a control.

Test strip C: This contains a mixture of methylated benzidine derivatives prepared in Reference Example 3 or in Reference Example 4.

Test strip D: The test strip contains non-treated benzidine and was employed as control.

These test strips were tested by dipping each of them in a solution which was so adjusted that a particular amount of urine of the human adult contained glucose in an amount as described in a table below and then by taking it out of the liquid sample immediately after being dipped therein. The color shade of the tested test strips was then compared in 60 to 120 seconds by referring to the standard color shade index and determined. The results are shown as follows:

Table 3

| Test Strips | Glucose Concentration, percent | | | |
| --- | --- | --- | --- | --- |
| | 0.1 | 0.25 | 0.5 | 2.0 |
| A | Yellowish green | Green | Greenish blue | Dark blue |
| B | Yellowish green | Greenish brown | Green-bluish brown | Bluish brown |
| C | Yellowish green | Green | Greenish blue | Blue |
| D | Yellowish brown | Greenish brown | Dark greenish brown | Brownish blue |

Note: Test strips B and D turned brown immediately after being taken out from the test sample.

With the same test strips as above, a test was conducted using a serum sample containing glucose in an amount from 0 to 120 mg. per dl. The test results were almost the same as above.

EXAMPLE 5

Various impregnating solutions were prepared containing a preferred combination of the following composition:

| Composition | Amounts |
| --- | --- |
| Mixture of the reaction products from ortho-tolidine (prepared in Reference Example 1 or 2) | 20 – 100 mg. |
| 95% ethanol | 4 – 8 ml. |
| 0.2 M citric acid buffer solution (pH 5.5) | 3 – 7 ml. |
| Tartrazine | 0.1 – 0.5 mg. |
| 10% Tween 20 | 0.05 – 0.5 ml. |

To a solution of 60 mg. of said mixture of the reaction products in 6 ml. of ethanol and 5 ml. of the buffer solution were added 0.2 mg. of tartrazine and 0.05 ml. of Tween 20 in this order. The strips were prepared in the same manner as in Example 4.

A solution in which non-treated ortho-tolidine was employed instead of said mixture of the reaction products was prepared in the same manner as above as a control solution.

The test strips were then adjusted by the same procedure as in Example 4. Of these, the test strip comprising a 5 × 40 mm. filter paper and containing a mixture of the reaction products prepared in Reference Example 1 (hereinbelow referred to as test strip E) and the other having the same construction as test strip E but containing unreacted ortho-tolidine instead of said mixture (hereinbelow referred to as test strip F) were tested: each of the test strips was dipped in a liquid sample which was adjusted by adding human blood to urine of a healthy human adult so as to have a concentration as described in the table below. The test strips were taken out of the liquid sample immediately thereafter and a drop of a 3 percent solution of hydrogen peroxide was dropped on the surface thereof. The color shade of the test strips was determined 30 seconds after addition thereto of the hydrogen peroxide solution. The results are shown as follows:

Table 4

| Test strip | Concentration of Occult Bleeding | | | | |
| --- | --- | --- | --- | --- | --- |
| | 1/100,000 | 1/20,000 | 1/10,000 | 1/2,000 | 1/1,000 |
| E | Yellowish green | Light green | Light blue | Dark green | Dark blue |
| F | Light yellowish | Yellowish green | Light blue | Blue | Dark blue |

Table 4-continued

| Test strip | Concentration of Occult Bleeding | | | | |
|---|---|---|---|---|---|
| | 1/100,000 | 1/20,000 | 1/10,000 | 1/2,000 | 1/1,000 |
| | green | | | | |

Note: The color shade of the test strip E was sharper and clearer than that of the test Strip F, thereby making it easier to distinguish one concentration over the other even if the color is in the same category.

EXAMPLE 6

A test strip comprising a sheet of paper and the alkylated ortho-tolidine of the present invention was prepared for use in examining the occult bleeding in solid excrements.

An impregnating solution having the following composition was prepared in a conventional manner:

| Composition | Amounts |
|---|---|
| Mixture of the reaction products prepared in Reference Example 1 | 240 mg. |
| Ethyl alcohol | 13 ml. |
| Guaiac | 40 mg. |
| Potassium dihydrogen phosphate | 180 mg. |
| Sodium hydrogen phosphate | 340 mg. |
| Tartrazine | 2 mg. |
| Water | 16 ml. |

As an alternative impregnating solution, the mixture of the reaction products of the alkylated ortho-tolidine or benzidine may also be employed without separation from the reaction mixture. A solution containing said mixture was prepared: 1.0 g. of ortho-tolidine was dissolved at 50° C. in 20 ml. of methyl alcohol (or ethyl alcohol); 0.6 g. of dimethyl sulfate was added; and the resulting mixture was left to stand for 30 to 60 minutes at room temperature and diluted with ethyl alcohol to a total volume of 54 ml. The impregnating solution had the following composition:

| Composition | Amounts |
|---|---|
| Said solution containing alkylated ortho-tolidines | 13 ml. |
| Guiaic | 40 ml. |
| Potassium disodium phosphate | 180 mg. |
| Disodium hydrogen phosphate | 340 mg. |
| Sodium hydroxide | 0 – 46 mg. |
| Tartrazine | 2 mg. |
| Water | 16 ml. |

The test strips were prepared by impregnating a support such as paper in each of said impregnating solutions and then drying the impregnated support without exposure to light.

As a control, test strips were also prepared in the same manner except that an impregnating solution was adjusted so as to contain non-alkylated derivatives in said impregnating solutions instead of the alkylated derivative.

The test strips so prepared were tested for the coloring reaction using an aqueous solution containing 5 percent by weight of hydrogen peroxide and 35 percent by weight of alcohol. The test results show that the test strip of the present invention was found to be sensitive to a human fresh blood sample which was diluted with water to a 1/100,000 concentration, whereas the control test strip was sensitive to a 1/20,000 dilution of the blood sample with water.

EXAMPLE 7

This example illustrates a test strip of the present invention to be useful for the examination of galactose in urine.

A test strip was prepared by dipping a sheet of a diethylaminoethyl cellulose filter paper (Whatman DE81) in an impregnating solution and drying it at 40° C. as the first step and by dipping the dry paper in another impregnating solution and drying it at the same temperature as the second step. The test strip so prepared was stored at a low temperature without shedding light directly thereon.

The impregnating solution for the first step had the following composition:

| Composition | Amounts |
|---|---|
| 0.3 M citric acid buffer solution (pH 5.0) | 6 ml. |
| Methylated ortho-tolidines | 20 mg. |
| Ethyl alcohol | 6 ml. |
| Tartrazine | 1 mg. |

The following solution was employed for the second step:

| Composition | Amounts |
|---|---|
| Galactose oxidase | 1,500 units |
| Peroxidase | 6 mg. |
| 0.1 M phosphate buffer solution (pH 7.0) | 6 ml. |

The test strip was found to be able to identify semiquantitatively galactose in urine in an amount ranging from 50 to 1,000 mg. per dl.

EXAMPLE 8

This example illustrates a test strip comprising the alkylated ortho-tolidines to be used for the identification of galactose in blood.

A test strip was prepared in the same manner as in Example 7 except for using two impregnating solutions having different compositions.

The composition of the impregnating solution for the first step was as follows:

| Composition | Amounts |
|---|---|
| 0.3 M phthalic acid buffer solution (pH 6.5) | 2.5 ml. |
| Polyvinyl alcohol | 20 mg. |
| Galactose oxidase | 1,500 units |
| Tartrazine | 0.4 mg. |
| Peroxidase | 1 mg. |

The impregnating solution used in the second step had the following composition:

| Composition | Amounts |
|---|---|
| Methylated ortho-tolidines | 80 mg. |
| Guaiac | 100 mg. |
| Ethyl alcohol | 13 ml. |

The test strip so prepared was tested in the same manner as above where glucose in blood was examined and it was found to identify semiquantitatively galactose in blood in a concentration of 40 to 500 mg. per dl.

It was also found that a test strip which was prepared in the same manner but wherein ortho-tolidine was employed instead of said mixture of the alkylated derivatives was inferior in the semiquantative analysis of galactose in blood to that prepared as above according to the present invention.

What we claim is:

1. A diagnosing instrument for detecting or measuring occult bleeding in urine or solid excrement comprising a mixture of diamino-biphenyl derivatives having alkyl substituents in the phenyl groups thereof and in which at least one of the hydrogen atoms in either of the amino groups thereof is substituted by at least one lower alkyl group having from one to four carbon atoms, supported on a bibulous, porous support.

2. A diagnosing instrument for detecting or measuring occult bleeding in urine or solid excrement comprising (1) a mixture of diamino-biphenyl derivatives having alkyl substituents in the phenyl groups thereof and in which at least one of the hydrogen atoms in either of the amino groups thereof is substituted by at least one lower alkyl group having from one to four carbon atoms and (2) a non-alkylated diamino-biphenyl derivative, supported on a bibulous, porous support.

3. The diagnosing instrument according to claim 2, wherein the lower alkyl group has from one to two carbon atoms.

4. The diagnosing instrument according to claim 2, wherein the diamino-biphenyl derivative is N-methyl-, N,N-dimethyl-, N,N'-dimethyl-, N,N,N'-trimethyl- or N,N,N',N'-tetramethyl-ortho-tolidine.

5. The diagnosing instrument according to claim 2, wherein the diamino-biphenyl derivative is N-ethyl, N,N-diethyl-, N,N'-diethyl-, N,N,N'-triethyl- or N,N,N',N'-tetraethyl-ortho-tolidine.

6. The diagnosing instrument according to claim 2, wherein the bibulous, porous support is filter paper, hardened filter paper, a sintered porous glass material or a sintered porous plastic material.

7. The diagnosing instrument according to claim 2, wherein the diamino-biphenyl derivative is tolidine in which at least one of the hydrogen atoms in either of the amino groups thereof is substituted by at least one lower alkyl group having from one to four carbon atoms.

8. The diagnosing instrument according to claim 2, wherein the diamino-biphenyl derivative is ortho-tolidine in which at least one of the hydrogen atoms in either of the amino groups thereof is substituted by at least one lower alkyl group having from one to four carbon atoms.

9. The diagnosing instrument according to claim 2, which additionally contains a guaiac.

10. The diagnosing instrument according to claim 9, wherein the guaiac is alpha-guaiaconic acid or beta-guaiaconic acid.

11. The diagnosing instrument according to claim 2, which additionally contains a buffer, a surfactant, a background adjusting dye or an agent for increasing the viscosity of the composition.

12. The diagnosing instrument according to claim 11, wherein the buffer is an aqueous solution of phthalic acid, a phosphate or citric acid.

13. The diagnosing instrument according to claim 11, wherein the background adjusting dye is tartrazine.

14. The diagnosing instrument according to claim 11, wherein the agent for increasing the viscosity is a protective colloid.

15. The diagnosing instrument according to claim 14, wherein the protective colloid is a polyalkylene glycol or polyvinyl alcohol.

16. A diagnostic method for detecting or measuring occult bleeding in urine or solid excrement which comprises applying a specimen of urine or solid excrement onto an instrument comprising (1) a mixture of diamino-biphenyl derivatives having alkyl substituents in the phenyl groups thereof and in which at least one of the hydrogen atoms in either of the amino groups thereof is substituted by at least one lower alkyl group having from one to four carbon atoms and (2) a non-alkylated diamino-biphenyl derivative as a chromogen supported on a bibulous, porous support, applying hydrogen peroxide thereto and observing the color change of the instrument.

17. The diagnostic method according to claim 16, wherein the lower alkyl group has from one to two carbon atoms.

18. The diagnostic method according to claim 16, wherein the diamino-biphenyl derivative is N-methyl-, N,N'-dimethyl-, N,N,N'-trimethyl- or N,N,N',N'-tetramethyl-ortho-tolidine.

19. The diagnostic method according to claim 16, wherein the diamino-biphenyl derivative is N-ethyl-, N,N-diethyl-, N,N'- diethyl-, N,N,N'-triethyl- or N,N,N',N'-tetraethyl-ortho-tolidine.

20. The diagnostic method according to claim 16, wherein said instrument additionally contains a buffer, a surfactant, a background adjusting dye or an agent for increasing the viscosity of the composition.

21. The diagnostic method according to claim 10, wherein the buffer is an aqueous solution of phthalic acid, a phosphate or citric acid.

22. The diagnostic method according to claim 16, wherein the background adjusting dye is tartrazine.

23. The diagnostic method according to claim 16, wherein the bibulous, porous support is filter paper, hardened filter paper, a sintered porous glass material or a sintered porous plastic material.

24. The diagnostic method according to claim 16, wherein the diamino-biphenyl derivative is tolidine in which at least one of the hydrogen atoms in either of the amino groups thereof is substituted by at least one lower alkyl group having from one to four carbon atoms.

25. The diagnostic method according to claim 16, wherein the diamino-biphenyl derivative is ortho-tolidine in which at least one of the hydrogen atoms in either of the amino groups thereof is substituted by at least one lower alkyl group having from one to four carbon atoms.

26. The diagnostic method according to claim 16, wherein said instrument additionally contains a guaiac.

27. The diagnostic method according to claim 26, wherein the guaiac is alpha-guaiaconic acid or beta-guaiaconic acid.

28. The diagnostic method according to claim 16, wherein the agent for increasing the viscosity is a protective colloid.

29. The diagnostic method according to claim 28, wherein the protective colloid is a polyalkylene glycol or polyvinyl alcohol.

* * * * *